(12) United States Patent
Deladi (10) Patent No.: US 10,307,136 B2
(45) Date of Patent: Jun. 4, 2019

(54) MONITORING APPARATUS

(71) Applicant: KONINKLIJKE PHILIPS N.V., Eindhoven (NL)

(72) Inventor: Szabolcs Deladi, Veldhoven (NL)

(73) Assignee: Koninklijke Philips N.V., Eindhoven (NL)

(*) Notice: Subject to any disclaimer, the term of this patent is extended or adjusted under 35 U.S.C. 154(b) by 462 days.

(21) Appl. No.: 14/908,181

(22) PCT Filed: Aug. 18, 2014

(86) PCT No.: PCT/EP2014/067578
§ 371 (c)(1),
(2) Date: Jan. 28, 2016

(87) PCT Pub. No.: WO2015/024907
PCT Pub. Date: Feb. 26, 2015

(65) Prior Publication Data
US 2016/0166231 A1    Jun. 16, 2016

(30) Foreign Application Priority Data
Aug. 21, 2013 (EP) ..................................... 13181129

(51) Int. Cl.
*A61B 8/00* (2006.01)
*A61B 8/08* (2006.01)
(Continued)

(52) U.S. Cl.
CPC .......... *A61B 8/0883* (2013.01); *A61B 8/0858* (2013.01); *A61B 8/12* (2013.01);
(Continued)

(58) Field of Classification Search
CPC ..... A61B 8/0883; A61B 8/488; A61B 8/5223; A61B 8/486; A61B 8/0858; A61B 8/12;
(Continued)

(56) References Cited

U.S. PATENT DOCUMENTS

| 7,672,706 B2 * | 3/2010 | Sathyanarayana ... A61B 5/0215 600/407 |
| 8,628,473 B2 | 1/2014 | Silwa et al. |

(Continued)

FOREIGN PATENT DOCUMENTS

JP    2012515013    7/2012

*Primary Examiner* — Joel Lamprecht (57) ABSTRACT

The present invention relates to a monitoring apparatus (100, 200) for monitoring a structural change in an object (280, 340), such as a heart wall tissue. Tissue at first and second locations exhibits first and second velocities. The monitoring apparatus (100, 200) comprises an ultrasound signal providing unit for providing ultrasound signals of the object (280, 340) for different times. The monitoring apparatus (100, 200) further comprises a discontinuity determination unit (120, 220) for determining a discontinuity of the first and second velocities based at least in part on a change in time of tissue velocity differences and of tissue velocity sums. From the discontinuity an ablation depth can be determined, which is an important parameter while performing an ablation procedure. For example, it can be used for determining the progress of ablation within the object and for determining when the ablation has reached a desired dimension.

13 Claims, 7 Drawing Sheets

(51) Int. Cl.
*A61B 8/12* (2006.01)
*A61B 18/14* (2006.01)
*A61B 18/00* (2006.01)
*A61B 90/00* (2016.01)

(52) U.S. Cl.
CPC .............. *A61B 8/486* (2013.01); *A61B 8/488* (2013.01); *A61B 8/5223* (2013.01); *A61B 18/1492* (2013.01); *A61B 2018/00351* (2013.01); *A61B 2018/00577* (2013.01); *A61B 2018/00982* (2013.01); *A61B 2090/062* (2016.02); *A61B 2090/3784* (2016.02)

(58) Field of Classification Search
CPC ...... A61B 18/1492; A61B 2018/00351; A61B 2018/00982; A61B 2090/3784; A61B 2090/062; A61B 2018/00577
See application file for complete search history.

(56) References Cited

U.S. PATENT DOCUMENTS

| | | |
|---|---|---|
| 9,087,369 B2 | 7/2015 | Zuo et al. |
| 9,144,413 B2 | 9/2015 | Matsumura |
| 9,326,748 B2 | 5/2016 | Sumi |
| 9,808,323 B2 | 11/2017 | Barley et al. |
| 9,901,321 B2 | 2/2018 | Harks et al. |
| 2005/0283074 A1* | 12/2005 | Jackson ............. A61B 18/1492 600/439 |
| 2008/0097207 A1 | 4/2008 | Cai |
| 2009/0099563 A1* | 4/2009 | Ciaccio ................ A61B 5/1075 606/41 |
| 2011/0251529 A1 | 10/2011 | Petruzzello et al. |
| 2012/0004547 A1 | 1/2012 | Harks et al. |
| 2013/0116560 A1 | 5/2013 | Chen et al. |

* cited by examiner

MONITORING APPARATUS

CROSS-REFERENCE TO PRIOR APPLICATIONS

This application is the U.S. National Phase application under 35 U.S.C. § 371 of International Application Serial No. PCT/EP2014/067578, filed on Aug. 18, 2014, which claims the benefit of European Patent Application Serial No. 13181129.1, filed on Aug. 21, 2013. These applications are hereby incorporated by reference herein.

FIELD OF THE INVENTION

The invention relates to a monitoring apparatus, a monitoring method and a monitoring computer program for monitoring a structural change.

BACKGROUND OF THE INVENTION

WO 2010/082146 A1 discloses a monitoring apparatus for monitoring an ablation procedure. The monitoring apparatus comprises an ultrasound signal providing unit for providing an ultrasound signal and an ablation depth determination unit for determining an ablation depth from the provided ultrasound signal. Monitoring of the formation of lesions in the tissue is carried out by using ecogenicity change in contrast images.

In order to provide a conclusive diagnosis on the formation of lesions, more complex processing may be necessary.

SUMMARY OF THE INVENTION

It is an object of the present invention to provide a monitoring apparatus for monitoring a structural change in an object more accurately. It is a further object of the invention to provide a corresponding monitoring method and a corresponding monitoring computer program.

In a first aspect of the invention, a monitoring apparatus is presented for monitoring a structural change in an object, where the object comprises material at first and second locations along a depth direction within the object, where the material at the first location exhibits a first velocity, where the material at the second location exhibits a second velocity, the monitoring apparatus comprising:

an ultrasound signal providing unit for providing ultrasound signals of the object for different times, the ultrasound signals being indicative of the first and second velocities; and a discontinuity determination unit for determining a discontinuity of the first and second velocities based at least in part on a difference between the first velocity and the second velocity at a first time and at a second time, and further based at least in part on a sum of the first velocity and the second velocity at the first time and at the second time.

Herein, a discontinuity of the velocity profiles may, e.g., result from a structural change in the object. The discontinuity determination unit determines the discontinuity of the velocity profiles from the generated ultrasound signal by taking the sum of velocities into account as well. Thus, detection of very small discontinuities, which only account for very small changes of velocities, is possible. Further, an ablation depth may be determined directly from the generated ultrasound signal by evaluating the determined discontinuity in the velocity profile. The ablation depth is an important parameter while performing an ablation procedure. For example, it can be used for determining the progress of ablation within the object and for determining when the ablation depth has reached a predefined value, in particular, when a predefined degree of transmurality has been reached, when related to an object with finite thickness delimited by a back wall, in particular, a wall of a heart. The ablation depth can particularly be used for determining when cardiac tissue has become transmural. By determining the ablation depth from the ultrasound signal, an important parameter of ablation is accurately determined, thereby improving the accuracy of monitoring the ablation procedure.

Two examples for generally known techniques in the ultrasound field available and commonly known to the skilled person to determine velocity fields are given in the following:

Speckle Tracking Echocardiography (STE) is an echocardiographic imaging technique that analyzes the motion of tissues in the heart by using ultrasonic sound waves.

"Doppler" synonymous with "velocity measurement" in medical imaging. Note that in many cases it is not the frequency shift (Doppler shift) of the received signal that is measured, but the phase shift (when the received signal arrives). For instance, one may use the local phase shift between two consecutive lines (or line groups) acquired in time. Individual lines are giving the field of depth (space) and originating from the individual driving pulses, and on the temporal axis the number of adjacent individual lines is determined by the pulse repetition rate. Assuming the pulse repetition rate is high enough for not causing aliasing, then the velocity is related to the local phase shift by $$v = \frac{\Phi}{\pi} \cdot \frac{c \cdot f_p}{4 f_c},$$

where $\Phi$ corresponds to the local phase shift, $f_p$ to the pulse repetition rate, $f_c$ corresponds to the central frequency of the ultrasound transducer, and c corresponds to the speed of sound in the tissue.

There have been research efforts with both techniques for ablation procedures. In general, the velocity field is not giving sufficient sensitivity to easily detect lesion formation during ablation. Therefore, the claimed invention defines the technique to increase the sensitivity to lesion formation based on eliminating the weakness of the velocity field or that of the simple strain rate analogy. Both techniques, i.e., Speckle Tracking Echocardiography (STE) and "Doppler measurement" yield essentially the same result.

The discontinuity of the first and second velocities may refer to a spatial discontinuity. Additionally and/or alternatively, the discontinuity of the first and second velocities may refer to a temporal discontinuity.

If an ultrasound pulse is sent out to the object, the ultrasound pulse is reflected at different depths such that echo signals are received by the ultrasound unit at different times. The echo signals, which are generated by reflection of the ultrasound pulse at different depths within the object, form an echo series. By considering the speed of sound and the time, when an echo is recorded after the ultrasound pulse has been sent out into the object, the echo series can be translated into a dependence of an ultrasound reflection property of the object on the depth within the object.

Furthermore, several ultrasound pulses are sent out to the object at different times, thereby generating echo series at different times. These echo series, which are obtained from different ultrasound pulses at different times and, thus, which belong to different times, form dynamic echo series. The ultrasound signal which depends on the received dynamic echo series represents therefore the ultrasound reflection properties of the object at different depths and at different times.

By performing the ablation procedure preferentially a lesion is generated in the object. The ablation depth is preferentially defined by the boundary of the lesion within the object.

By determining the ablation depth at different times, the progression of ablation, in particular, the progression of the lesion boundary indicating the ablation depth can be determined The object is preferentially a heart wall, wherein the tissue of the heart wall is ablated.

The ultrasound signal providing unit can be any unit that provides the ultrasound signal. For example, the ultrasound signal providing unit can be a storing unit in which produced ultrasound signals are stored or it can be an ultrasound signal receiving unit for receiving a generated ultrasound signal as an input which can be used by the discontinuity determination unit for determining the ablation depth from the generated ultrasound signal.

It is preferred that the discontinuity determination unit is adapted to determine a discontinuity of the velocity profile based on the ultrasound signal. From the discontinuity, the ablation depth may be determined as the depth of the ultrasound signal at which the discontinuity occurs. In particular, the provided ultrasound signal represents ultrasound reflection properties of the object at different depths and at different times, wherein the discontinuity determination unit is adapted to determine a discontinuity of the velocity profile based on the ultrasound signal such that the ablation depth may be determined as the depth of the ultrasound signal at which the discontinuity occurs.

A discontinuous variation can easily be distinguished from a continuous variation which generally relates to macroscopic tissue expansion. Thus, the determination of the ablation depth depending on discontinuities allows easily and accurately determining the ablation depth.

The ultrasound signal that depends on the received dynamic echo series can be represented as a two-dimensional image showing a reflection intensity depending on two-dimensions, for example, depending on the time on a horizontal axis and depending on the depth on a vertical axis. This two-dimensional image can also be regarded as an M-mode image. The discontinuity determination unit can be adapted to determine discontinuities in this two-dimensional image, wherein the ablation depth at a certain time is further determined by determining the position in the two-dimensional image, at which the discontinuity has been determined. The ultrasound signal that depends on the received dynamic echo series can also be represented as a three- or four-dimensional image showing a reflection intensity depending on the time and two or three spatial dimensions, respectively. This allows determining the ablation depth in different directions in which ultrasound pulses have been sent out into the object.

In an embodiment, the discontinuity determination unit is configured to determine the discontinuity based at least in part on an expression of the form $(v(t_j, x_i) - v(t_j, x_{i-1}))^a (v(t_j, x_i) + v(t_j, x_{i-1}))^b$, wherein $v(t_j, x_i)$ corresponds to the first velocity at the first location $x_i$ at the first time $t_j$, $v(t_j, x_{i-1})$ corresponds to the second velocity at the second location $x_{i-1}$ at the first time $t_j$ and b is not equal to zero. By employing exponents a and b, the difference term $v(t_j, x_i) - v(t_j, x_{i-1})$ and the sum term $v(t_j, x_i) + v(t_j, x_{i-1})$ may be weighted respectively to adapt visual perception, e.g., in regions where only very small velocity changes occur such that the difference term would be very small. In particular, b is equal to or larger than a. By choosing a larger exponent for the sum term than for the difference term, very small changes of velocity differences may still be detected. In particular, a is less than zero. Further, in particular, b is larger than one.

In a further preferred embodiment, the monitoring apparatus further comprises a velocity determination unit for determining the first and second velocities from the ultrasound signals of the object for different times. The velocity determination unit may be separate from or integrated in one of the other components of the monitoring apparatus. For instance, the velocity determination unit may be integral to the discontinuity determination unit. As another example, the velocity determination unit may be separate from the discontinuity unit and provide the respective velocity information to the discontinuity determination unit. Example approaches for determining the velocities have been given above, and comprise, e.g., Speckle Tracking Echocardiography (STE) and/or "Doppler velocity measurement". It is however not essential which method is used to determine the velocities.

In a further preferred embodiment, the discontinuity determination unit is adapted to determine a discontinuity of the first and second velocities by evaluating the difference between the first velocity and the second velocity at the first time and at the second time, and by further evaluating the sum of the first velocity and the second velocity at the first time and at the second time.

In an embodiment, the discontinuity determination unit is further configured to determine the discontinuity based at least in part on an expression of the form $$\frac{(v(t_j, x_i) - v(t_j, x_{i-1}))^a (v(t_j, x_i) + v(t_j, x_{i-1}))^b}{(x_i - x_{i-1})^c},$$

where c is not equal to zero. The above expression allows for a straightforward comparison of previous measurements based on the strain rate analogy by letting a→1, b→0, c→1. This way, a user may have more flexibility in choosing parameters best suited for the respective application. Parameters may be chosen, e.g., depending on material behavior or on the applied external load.

In an embodiment, the ultrasound signal providing unit comprises an ultrasound unit for
  sending ultrasound pulses out to the object,
  receiving dynamic echo series after the ultrasound pulses have been sent out to the object,
  generating an ultrasound signal depending on the received dynamic echo series.

If an ultrasound pulse is sent out to the object, the ultrasound pulse is reflected at different depths such that echo signals are received by the ultrasound unit at different times. The echo signals, which are generated by reflection of the ultrasound pulse at different depths within the object, form an echo series. By considering the speed of sound and the time, when an echo is recorded after the ultrasound pulse has been sent out into the object, the echo series can be translated into a dependence of an ultrasound reflection property of the object on the depth within the object. Furthermore, several ultrasound pulses are sent out to the object at different times, thereby generating echo series at different times. These echo series, which are obtained from different ultrasound pulses at different times and, thus, which belong to different times, form dynamic echo series. The ultrasound signal which depends on the received dynamic echo series represents therefore the ultrasound reflection properties of the object at different depths and at different times.

In an embodiment, the object is a tissue wall to which energy is applied for influencing the tissue wall such that the ultrasound signal providing unit provides ultrasound signals of the tissue wall for different times. The object is preferentially a heart wall, wherein the tissue of the heart wall is ablated. By examining ultrasound signals of the tissue wall for different times, an ablation of the heart wall can be monitored. Thus, safety of the ablation procedure is improved, because the procedure may be stopped as soon as or before the lesion has become transmural.

In an embodiment, the monitoring apparatus further comprises a sensing probe, in which the ultrasound signal providing unit and an energy application unit for applying energy to the object are integrated. The sensing probe is preferentially a catheter, in which at least a part of the ultrasound signal providing unit, for instance, one or several ultrasound transducers, and at least a part of the energy application unit, for instance, an ablation electrode, are integrated. Thus, a single sensing probe may be provided, which can be used for applying energy to the object, in particular, for performing a cardiac ablation procedure, and for monitoring the application of the energy by using ultrasound.

In an embodiment, the ultrasound signals represent ultrasound reflection properties of the object at different depths and at different times, wherein the monitoring apparatus further comprises an ablation depth determination unit adapted to determine an ablation depth as the depth of the ultrasound signals at which the discontinuity occurs. A discontinuous variation can easily be distinguished from a continuous variation which generally relates to macroscopic tissue expansion. Thus, the determination of the ablation depth depending on discontinuities allows easily and accurately determining the ablation depth. The ultrasound signal that depends on the received dynamic echo series can be represented as a two-dimensional image showing a reflection intensity depending on two-dimensions, for example, depending on the time on a horizontal axis and depending on the depth on a vertical axis. This two-dimensional image can also be regarded as an M-mode image. The ablation depth determination unit can be adapted to determine discontinuities in this two-dimensional image, wherein the ablation depth at a certain time is determined by determining the position in the two-dimensional image, at which the discontinuity has been determined. The ultrasound signal that depends on the received dynamic echo series can also be represented as a three- or four-dimensional image showing a reflection intensity depending on the time and two or three spatial dimensions, respectively. This allows determining the ablation depth in different directions in which ultrasound pulses have been sent out into the object.

In an embodiment, the object is a wall, wherein the apparatus is adapted to determine the thickness of the wall and repeatedly the ablation depth, wherein the ablation depth determination unit is adapted to determine repeatedly a degree of transmurality of ablation from the determined thickness and the determined ablation depth. In particular, the apparatus is adapted to terminate an ablation procedure, if a predetermined degree of transmurality of ablation has been reached. If the thickness of the wall is modified, for example, by the ablation procedure, preferentially also the determination of the thickness of the wall is also performed repeatedly.

In an embodiment, the object is a wall, wherein the ablation depth determination unit is adapted to determine the position of a front surface and a back surface of the wall from the ultrasound signals, and wherein the ablation depth determination unit is adapted to determine the thickness of the wall from the determined positions of the front surface and the back surface of the wall. Thus, the ultrasound signal can be used for determining the ablation depth and for determining the thickness of the wall, which is preferentially a wall of a heart, i.e. it is for example not necessary to provide a further unit for measuring the wall thickness. The thickness of the wall, the ablation depth and the degree of transmurality can be determined by using the ultrasound signal only. Furthermore, since the ablation depth determination unit is adapted to determine the thickness of the wall from the ultrasound signal, an ablation procedure can be planned based on this determined thickness.

In another aspect of the present invention, a monitoring method for monitoring a structural change in an object is presented, where the object comprises material at first and second locations along a depth direction within the object, where the material at the first location exhibits a first velocity, where the material at the second location exhibits a second velocity, the monitoring method comprising the steps of:

providing ultrasound signals of the object for different times by an ultrasound signal providing unit, the ultrasound signals being indicative of the first and second velocities, determining a discontinuity of the first and second velocities by evaluating a difference between the first velocity and the second velocity at a first time and at a second time, and by further evaluating a sum of the first velocity and the second velocity at the first time and at the second time. Herein, a discontinuity of the velocity profiles may, e.g., result from a structural change in the object.

In another aspect of the present invention, monitoring computer program for monitoring a structural change in an object, the monitoring computer program comprising program code means for causing a monitoring apparatus according to the present invention to carry out the steps of the monitoring method according to the present invention, when the computer program is run on a computer controlling the monitoring apparatus.

It shall be understood that the monitoring apparatus of claim 1, the monitoring method and the monitoring computer program of claim 13 have similar and/or identical preferred embodiments as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
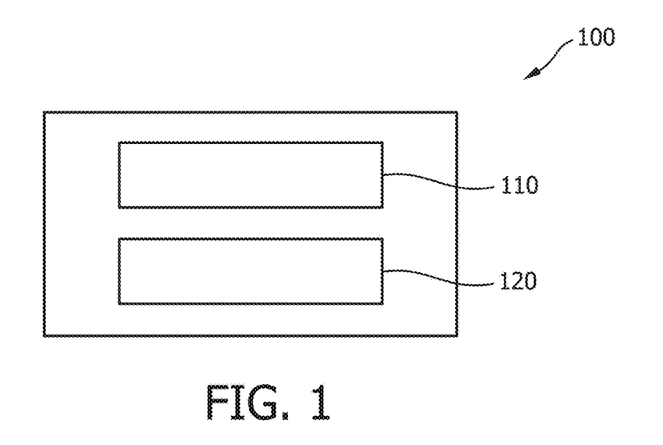
FIG. 1 shows schematically and exemplarily an embodiment of a monitoring apparatus for monitoring a structural change in an object.

FIG. 1 shows schematically and exemplarily a monitoring apparatus 100 for monitoring a structural change in an object. The monitoring apparatus 100 comprises an ultrasound signal providing unit 110 for providing an ultrasound signal produced by sending ultrasound pulses out to the object, receiving dynamic echo series after the ultrasound pulses have been reflected by the object and generating the ultrasound signal depending on the received dynamic echo series. The ultrasound signal providing unit 110 is, for example, a storing unit in which the ultrasound signals are stored for providing them, or the ultrasound signal providing unit is, for example, an ultrasound signal receiving unit for receiving ultrasound signals from an ultrasound unit and for providing these ultrasound signals. The ultrasound signal providing unit 110 can also be an ultrasound unit for producing the ultrasound signals.

The monitoring apparatus 100 further comprises a discontinuity determination unit 120 for determining a discontinuity of the velocity profile based on ultrasound signals.

If an ultrasound pulse is sent out to the object, the ultrasound pulse is reflected at different depths such that echo signals are received by an ultrasound unit. The echo signals, which are generated by reflection of the ultrasound pulse at different depths within the object, form an echo series. By considering the speed of sound and the time, at which an echo is recorded after the ultrasound pulse has been sent out to the object, the echo series can be translated into a dependence of an ultrasound reflection property of the object on the depths within the object.

Figure 2:
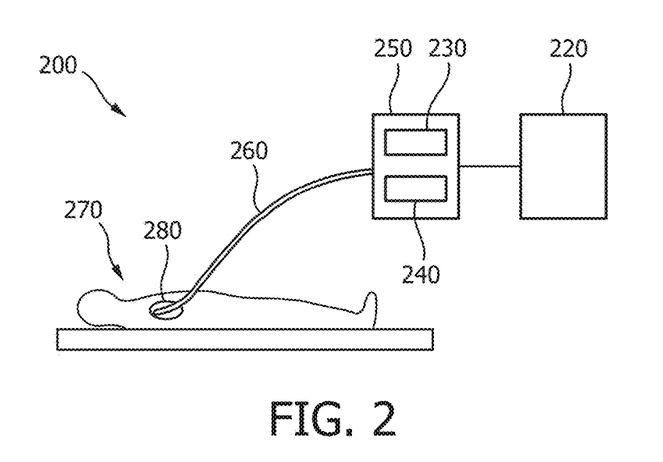
FIG. 2 shows schematically and exemplarily another embodiment of a monitoring apparatus for monitoring a structural change in an object.

FIG. 2 shows schematically and exemplarily another embodiment of a monitoring apparatus 200 for monitoring an ablation procedure applied to an object. The monitoring apparatus 200 comprises an ultrasound unit at a distal end of a catheter 260, i.e. at a catheter tip 310, which is shown in more detail in FIG. 3. The ultrasound unit (not shown in FIG. 2) is an ultrasound signal providing unit and controlled by an ultrasound control unit 230. The ultrasound unit and the ultrasound control unit 230 are adapted to send out ultrasound pulses to an object 280, to receive dynamic echo series after the ultrasound pulses have been reflected by the object and to generate the ultrasound signal depending on the received dynamic echo series. The object 280 is, in this embodiment, heart wall tissue of a patient 270 to whom an ablation procedure is applied. In another embodiment, the ablation of another object like another organ of a person or of an animal or of a technical object can be monitored by the monitoring apparatus.

At the distal end of the catheter 260 an ablation unit for ablating object 280 may be located. The ablation unit (not show in FIG. 2) comprises energy application elements like electrodes for applying electrical energy, in particular, radio-frequency energy, or like optical elements for applying light energy, for example, optical fibers and/or other optical elements. The electrodes are preferentially unipolar or bipolar. The energy application elements are preferentially arranged in a line or in a curve for ablating the object along a line or along a curve.

The monitoring apparatus 200 further comprises a sub-control unit 240 for controlling the ablation element. The sub-control unit 240 and the ultrasound control unit 230 are integrated in a control unit 250. In other embodiments, the control units can be separate control units. Furthermore, the sub-control unit 240 is preferentially further adapted to control a steering of the catheter tip, a sensing of the heart wall tissue and/or an irrigation. In this case, the catheter comprises a steering element, a sensing element and/or an irrigation element, respectively. These different control functions can be performed by any other number of control units, for example, by a single control unit or by two or more than two control units.

The monitoring apparatus 200 further comprises a discontinuity determination unit 220 for determining discontinuity from an ultrasound signal generated by the ultrasound unit. The discontinuity determination unit 220 is therefore adapted to receive an ultrasound signal from the ultrasound unit and to determine the discontinuity as described above with reference to the discontinuity determination unit 120, i.e. the discontinuity determination unit 120 and 220 are similar.

The sub-control unit 240 is adapted to control the ablation unit depending on the ablation depth determined by an ablation depth determination unit. For example, the power and/or duration of applying ablation energy to the object 280 are controlled depending on the determined ablation depth. The ablation depth determination unit is adapted to determine the position of a front surface and a back surface of the heart wall 280 from the ultrasound signal and to determine the thickness of the heart wall depending on these positions, i.e. the corresponding depth positions are subtracted from each other to determine the thickness of the heart wall. The sub-control unit 240 is adapted to control the ablation unit depending on this determined thickness and the determined ablation depth. Preferentially, the sub-control unit 240 is adapted to ablate the heart wall tissue until a desired degree of transmurality of the heart wall tissue is reached, in particular, until the resulting lesion is transmural.

Preferentially, the monitoring apparatus 200 is adapted to determine the thickness of the heart wall 280 and the ablation depth repeatedly, wherein the ablation depth determination unit is adapted to determine repeatedly a degree of transmurality of ablation from the determined thickness and the determined ablation depth. In particular, the monitoring apparatus 200 is adapted to terminate an ablation procedure, if a predetermined degree of transmurality of ablation has been reached.

Since the ablation depth determination unit is adapted to determine the thickness of the wall 280 from the ultrasound signal, an ablation procedure can be planned based on this determined thickness.

The monitoring apparatus 200 may further comprise a visualization unit (not shown in FIG. 2) for visualizing the discontinuity. In particular, the visualization unit is adapted for visualizing the progression of a lesion boundary. The visualization is preferentially performed in real-time. The visualization unit is preferentially adapted to show the ultrasound signal, the progression of ablation, i.e. the lesion boundary, and the front and back surface positions. The visualization unit can also be adapted to show the ablation depth by just reporting the percentage of transmurality over time.

The ultrasound unit can be adapted to direct ultrasound pulses in only one direction or periodically in different directions. For example, each ultrasound pulse can be regarded as an ultrasound beam, wherein the ultrasound beam is swept. Thus, echo series can be received in different directions for producing a spatially two- or three-dimensional ultrasound signal. The ablation depth determination unit is preferentially adapted to determine the heart wall thickness and the ablation depth at different x positions. Thus, the spatially two- or three-dimensional ultrasound signal is produced several times at different times, thereby producing a time-dependent spatially two- or three-dimensional ultrasound signal depending on the received dynamic echo series. This time-dependent spatially two- or three-dimensional ultrasound signal is used for determining the thickness of the heart wall and the ablation depth in different directions. This allows scanning a larger region of the heart wall tissue.

For producing the spatially two- or three-dimensional ultrasound signal, the ultrasound unit preferentially comprises a redirection element for redirecting the ultrasound pulses in different directions. The redirection element is, for example, a fluid lens, an electromechanical steering element, a mechanical rocker probe or another element for redirecting the ultrasound pulses. Furthermore, the redirection element can be integrated in a transducer of the ultrasound unit, for example, by using phased-array ultrasound transducers like a capacitive micro-machined ultrasound transducer or piezoelectric micro-machined ultrasound transducer.

Figure 3:
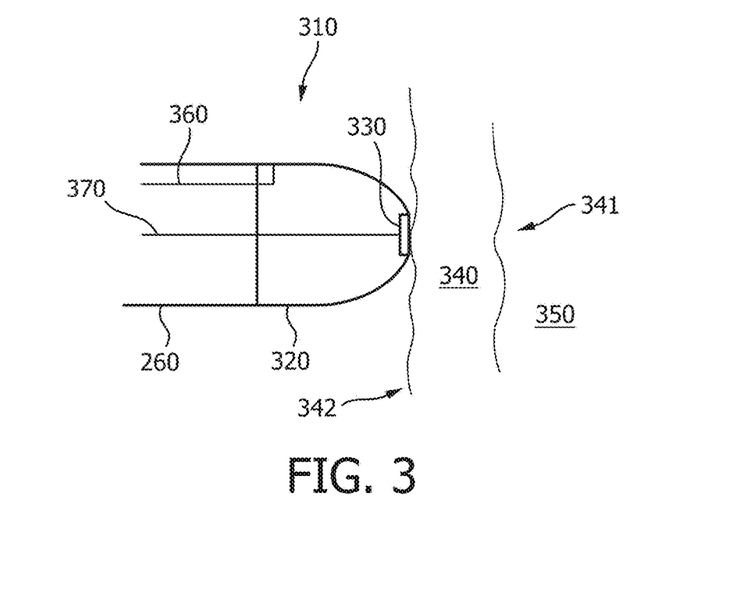
FIG. 3 shows schematically and exemplarily a tip of a catheter of the monitoring apparatus.

FIG. 3 shows schematically and exemplarily an embodiment of a tip of a catheter of the monitoring apparatus 100, 200. The catheter tip 310 comprises an ultrasound transducer 330, which is connected to an ultrasound control unit 230 for controlling the ultrasound transducer 330 via an electrical connection 370 like an insulated coaxial cable or a twisted pair of wires. The ultrasound transducer 330 and the ultrasound control unit 230 form an ultrasound signals providing unit for providing ultrasound signals of the tissue wall 340 for different times. In particular, the ultrasound transducer 330 and the ultrasound control unit 230 are adapted to send ultrasound pulses into the tissue wall 340, to receive echo series after the ultrasound pulses have been reflected by the tissue wall 340 and to generate A-lines depending on the received echo series. The ultrasound signal providing unit 110 acquires therefore temporally consecutively A-lines for providing ultrasound signals of the tissue wall 340 for different times, i.e. to each A-line a time can be assigned being the time at which the respective ultrasound pulse has been sent and received by the ultrasound signal providing unit 110.

The catheter tip 310 further comprises an energy application unit 320 being, in this embodiment, an RF ablation electrode for applying energy to the tissue wall 340. The catheter 260 forms therefore a sensing probe, in which the ultrasound transducer 330 and the RF ablation electrode 320 are integrated. The RF ablation electrode 320 is connected with an RF source via an electrical connection 360 like an insulated wire. The tissue wall 340 comprises an outer surface 341 and an outer surface 342. Further tissue may be present in a region 350 behind the tissue wall 340.

Figure 4:
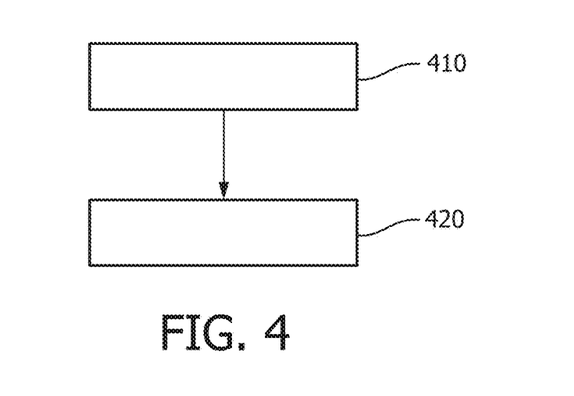
FIG. 4 shows a flowchart schematically and exemplarily illustrating an embodiment of a monitoring method for monitoring a structural change in an object.

In the following an embodiment of monitoring method for monitoring a structural change in an object, where the object comprises material at first and second locations within the object, where the material at the first location exhibits a first velocity, where the material at the second location exhibits a second velocity, will exemplarily be described with reference to a flowchart shown in FIG. 4.

In step 410, ultrasound signals of the object for different times are provided by an ultrasound signal providing unit.

In step 420, a discontinuity of the ultrasound signals is determined by evaluating a difference between the first velocity and the second velocity at a first time and at a second time, and by further evaluating a sum of the first velocity and the second velocity at the first time and at the second time.

In the following, a mathematical formulation of highlighting and making visually perceivable a difference between untreated and treated (such as, e.g., ablated) tissue is presented. In particular, a perceivable distinction between a first layer of interest for treatment and adjacent tissue structures is aimed for. The mathematical formulation may be applied, e.g., by discontinuity determination unit 120, 220 to determine a discontinuity of the ultrasound signals, from which in turn an ablation depth may be determined The technique is based on the velocity fields measured by ultrasound.

Figure 5:
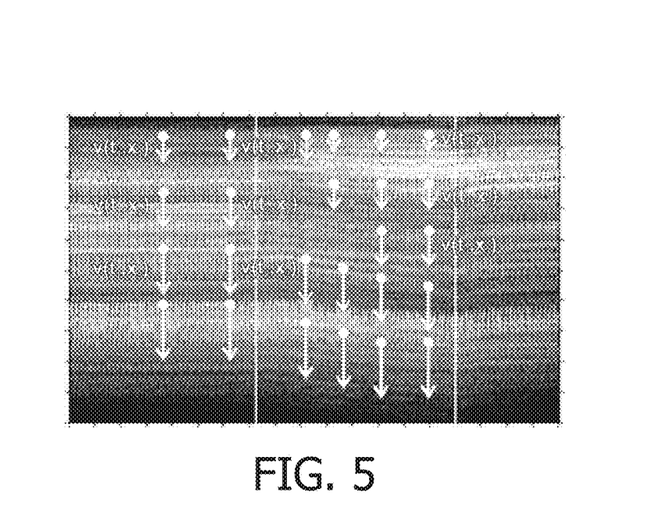
FIG. 5 shows a velocity field in an ultrasound M-mode image.

Velocity fields can be calculated from the displacement of structures in time with respect to an ultrasound transducer in the catheter tip. In case that the transducer in the catheter tip 310 is in direct contact with the cardiac tissue 340, the relative velocity of the tissue at the transducer face will be zero. The velocity of structures that are further away from catheter tip 310 varies with the depth of the tissue upon applied load between catheter and tissue. This is directly related to the material properties (such as, e.g., inhomogeneity, flexibility, etc). In most cases observed in bench studies and pre-clinical studies the velocity in the tissue increases with the depth of the tissue. Cardiac cycle and breathing motion result in a periodic relative motion between catheter and tissue. In FIG. 5, a velocity field is shown in an ultrasound M-mode image, where the velocity of points at 0 mm is zero due to the mechanical restraint resulting from the direct contact of catheter tip 310 with the tissue. The velocity of the tissue with respect to the catheter tip increases with depth in this case. Note that the velocity field is due to the cyclic nature of the load also cyclical.

As FIG. 5 illustrates, due to ablation inception where the tissue is heated, e.g., by RF energy applied, e.g. via energy application unit 320 though catheter tip 310, the upper part of the tissue in contact with catheter undergoes a structural change resulting in slight contrast changes, but also in slight changes of the velocity field. The slight contrast changes relate to the amount of ultrasound signal reflected back to transducer 330. Said contrast changes might be small and not very indicative that the tissue has undergone structural changes. However, the change of velocity of the tissue upon ablation is a much better indication of the structural change. The term "velocity field" generally corresponds to an assignment of a velocity $$\begin{pmatrix} v_1(x_1, \ldots, x_n) \\ \vdots \\ v_n(x_1, \ldots, x_n) \end{pmatrix}$$

to each point $$\begin{pmatrix} x_1 \\ \vdots \\ x_n \end{pmatrix}$$

in space (or to each point of a subset of a given space). FIG. 5 thus shows an assignment of a velocity $v_x(t, x)$ (indicated by arrows pointing downwards, where the error length illustrates the velocity magnitude) to each point $$\begin{pmatrix} t \\ x \end{pmatrix}$$

(indicated by bullets at the arrow's starting point) in a (t, x)-space.

For example, a certain structure in the tissue at a given depth might become slightly darker or lighter in the contrast image, but it does not give an immediate indication of its velocity. The velocity is a transformation of the signal, which eliminates the contrast intensity variation. Until a certain structure can be detected with ultrasound, no matter if it is strongly contrasted or less visible, the velocity will be independent of how intense the reflection is. A deeper structure always has to deal with what is happening in the superficial layer. In ultrasound applications, this effect is called "shadowing effect". Upon a slight change of transmission or scattering in the superficial layer, a slight contrast change in the deeper structure is imminent. This contrast change may give rise to misinterpretations. A practical example concerns ablation of a superficial layer 342. An ultrasound signal has to pass through superficial layer 342 first in order to reach deeper regions, and then, after being reflected, pass again through the superficial layer to be received by the transducer 330. A change in the superficial layer might give enough change to the ultrasound signal to result in deeper regions being perceived differently before and during the application of RF energy. A further potentially disturbing factor might be tissue expansion upon heating, which leads to an increase in the acoustic path. Since there is finite ultrasound attenuation in the tissue, any path length changes (i.e., even without structural change upon ablation) leading to the deeper layers being perceived differently before and during the tissue expansion.

This is a limitation of only using contrast images, where intensity variations based on ultrasound physics may result in misinterpretation.

However, considering the velocity of the structures encountered in tissue 340 provides a further dimension to the ablation monitoring technique. Ablation monitoring based on structural velocity is insensitive to an acoustic path change, except on the outer boundary 341, where an acoustic path change potentially might lead to the structure moving beyond the penetration depth (which, at 30 MHz, is ~8-9 mm in cardiac tissue). The structure becoming slightly darker or lighter does not affect its velocity in the calculations. Accordingly, the velocity field is better suited to monitor structural change in object 280 due to the velocity field's nature of being related to material properties. One example of a velocity based technique for distinguishing structural change is the "strain rate", as illustrated by FIG. 6.

Figure 6:
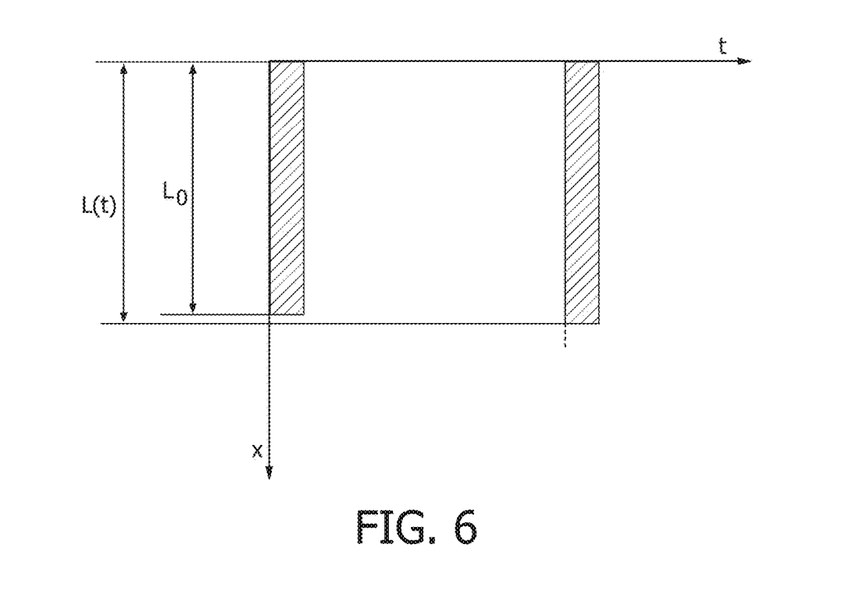
FIG. 6 illustrates the derivation of strain and strain rate according to the strain rate analogy.

Referring to FIG. 6, consider a bar with length $L_0$, which at a moment t will have a length of L(t). The strain $\varepsilon$ and strain rate $\dot{\varepsilon}$ are defined by $$\varepsilon(t) = \frac{L(t) - L_0}{L_0} \text{ and}$$

$$\dot{\varepsilon}(t) = \frac{d\varepsilon}{dt} = \frac{d}{dt}\left(\frac{L(t) - L_0}{L_0}\right) = \frac{1}{L_0}\frac{dL}{dt}(t) = \frac{v(t)}{L_0}.$$

In the present case, the velocities of points in depth (x axis) and in time (t axis) are potentially not equal.

Figure 7:
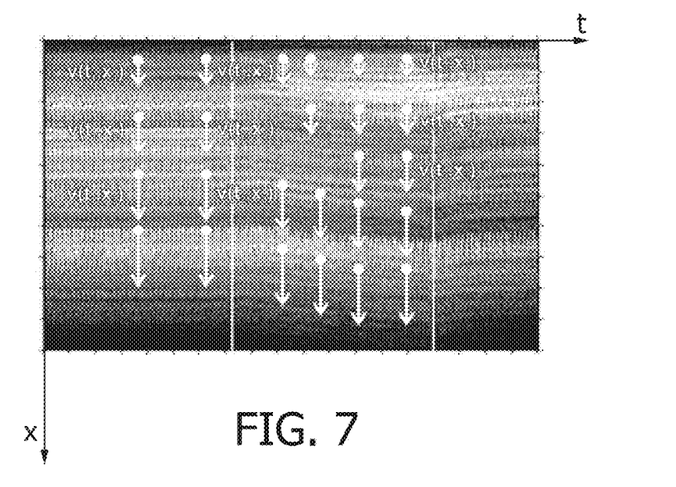
FIG. 7 illustrates the analogy of tissue ablation to the strain rate in material science.

An analogous mathematical formulation, which is illustrated by FIG. 7, reads:

$$s(t_j, x_i) = \frac{v(t_j, x_i) - v(t_j, x_{i-1})}{x_i - x_{i-1}} \quad \text{(Eq. 1)}$$

where $x_i$ represents position of a point along the x axis, and $t_j$ represents position of the point on the t axis.

Figure 8:
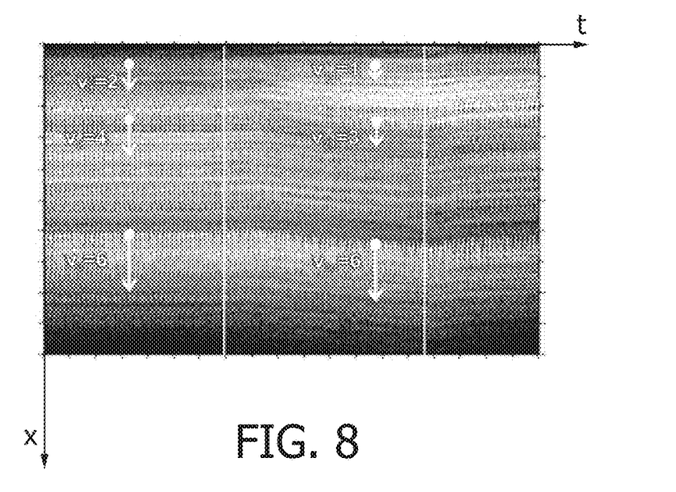
FIG. 8 shows an example to illustrate the limitation of the strain rate analogy in lesion detection.

As can be seen from Eq. 1, the strain rate analogy has a limitation in using it for lesion detection. Consider the example in FIG. 8. The drawing shows that velocity $v_1$ at point 1 amounts to "2" at a time before the start of ablation, and "1" during ablation. The drawing further shows that velocity $v_2$ at point 2 amounts to "4" at a time before the start of ablation, and "3" during ablation. The drawing further shows that velocity $v_3$ at point 3 amounts to "6" at a time before the start of ablation, and "6" during ablation. Assuming a unit distance between two respective points simply means that the term $x_i - x_{i-1}$ in Eq. 1 equals unity (i.e., "1") so that calculation of the strain rate simplifies to determining respective velocity differences. If the strain rate is calculated before and during ablation between points 1 and 2 situated at a unit distance, then the strain rate before and after ablation is equal (in value 2), whereas it is clear that there is a velocity difference of the points 1 and 2 before and during ablation. However, if the strain rate is calculated before and during ablation between points 2 and 3, then the strain rate before and after ablation is different, thereby differentiating the two points. To give further details with regard to the example given, the strain rate between points 1 and 2 before ablation (at time $t_1$) amounts to $$s(t_1, x_2) = \frac{v(t_1, x_2) - v(t_1, x_1)}{x_2 - x_1} = \frac{4-2}{1} = 2,$$

whereas the strain rate between points 1 and 2 during ablation (at time $t_2$) amounts to $$s(t_2, x_2) = \frac{v(t_2, x_2) - v(t_2, x_1)}{x_2 - x_1} = \frac{3-1}{1} = 2.$$

The strain rates before and after ablation when considering points 1 and 2 are thus equal.

In a similar manner, the strain rate between points 2 and 3 before ablation (at time $t_1$) amounts to $$s(t_1, x_3) = \frac{v(t_1, x_3) - v(t_1, x_2)}{x_3 - x_2} = \frac{6-4}{1} = 2,$$

whereas the strain rate between points 2 and 3 during ablation (at time $t_2$) amounts to $$s(t_2, x_3) = \frac{v(t_2, x_3) - v(t_2, x_2)}{x_3 - x_2} = \frac{6-3}{1} = 3.$$

The strain rates before and after ablation when considering points 2 and 3 are thus different.

As a consequence, only the lesion front boundary 342 is detected. This is an unpractical situation in clinical practice due to the real-time nature of the lesion monitoring. Namely, determining the strain rate according to (Eq. 1) may not detect a slight change occurring only at the boundary 342 of the lesion, leading to identical values for the thus calculated strain rate before, during, and after ablation. This constitutes a limitation for safety, sensitivity and specificity of the technique. Moreover, the sensitivity of the strain rate analogy is poor for slight changes of velocity fields. Another limitation is where adjacent structures have similar material properties, which would be the case for the catheter being in the atrium pointing downwards towards the ventricle, both being myocardium tissue. Ablating through the atrial tissue also the ventricular tissue from outside, without recognizing that there are two different structures, may cause myocardial infarct or other related serious complications.

The sensitivity of the strain rate analogy is very low to detect this type of discontinuity. This is true, even if the above-explained effect for certain velocity field differences is not taken into account.

In order to overcome the limitations of the ultrasound contrast based lesion monitoring, the lack of sensitivity of the velocity field based approach, as well as the weakness of the strain rate analogy approach, a new mathematical formulation has been developed and tested for the above mentioned limitations.

The approach is based on the observation that though the difference of velocities of neighboring points can be the same before and after ablation, the sum of them is different in case that structural change occurs due to ablation:

$$f(t_j, x_i) = \frac{A \cdot [v(t_j, x_i) - v(t_j, x_{i-1})]^a \cdot [v(t_j, x_i) + v(t_j, x_{i-1})]^b}{B}, \quad \text{(Eq. 2)}$$

wherein a and b are exponents to increase the dynamic range of sensitivity to discontinuities due to lesion formation and/or adjacent layers. The terms A and B may be constants or other terms related to the position of the structures the calculations are related to. For example:

$$B = D \cdot [x_i - x_{i-1}]^c \quad \text{(Eq. 3)},$$

wherein c is an exponent and D is a constant or an additional term.

If parameters A, D, a, c are equal to one and parameter b is equal to zero, then Eq. 2 becomes Eq. 1, which makes this scenario undesirable.

Figure 9:
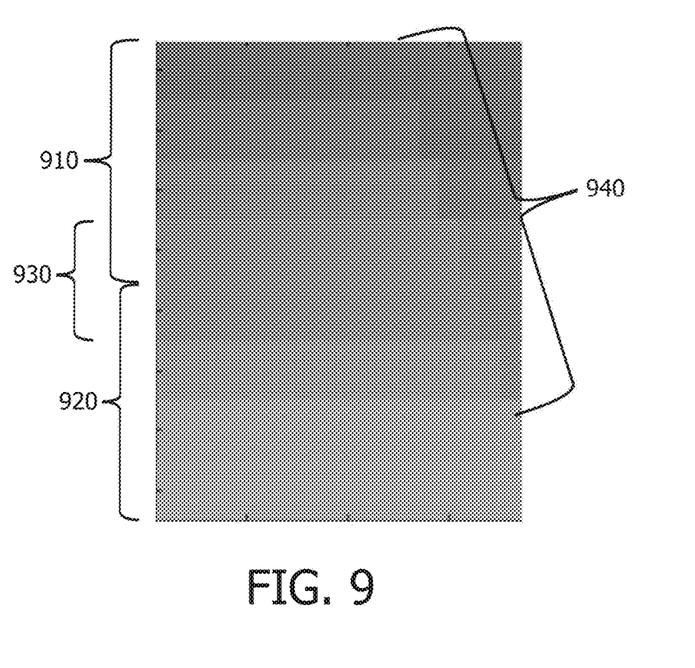
FIG. 9 shows a velocity field model used as an input to a simulation.

Simulations illustrating the potential of the new formulation have been carried out. The direct input for the algorithm was a velocity field as illustrated by FIG. 9. A first layer 910 is shown with increasing velocity in depth, i.e., having velocity values stepwise increasing with the depth of the tissue. At a certain depth, an interface 930 with a second layer 920 comprising a material having the same properties as layer 910 is provided. In second layer 920, velocities also increase with the depth of the tissue. Accordingly, at interface 930, the same incremental increase of the velocities in depth is exhibited. A further region 940 shows a velocity discontinuity in an upper right part of the velocity field. Region 940 corresponds to a lesion formation region. Discontinuity in velocity is smaller than the ablation, but increases with depth as well, and extends into second layer 920. Most notably, very small discontinuities have been used as lesion formation in lesion formation region 940.

By means of the simulations, the ability to visually differentiate between adjacent structures (first and second layers 910, 920 in the vertical direction) and to visually perceive a discontinuity between non-ablated and ablated regions (in the horizontal direction) is assessed. Simulation results are illustrated in FIGS. 10A to 10E.

Figure 10A:
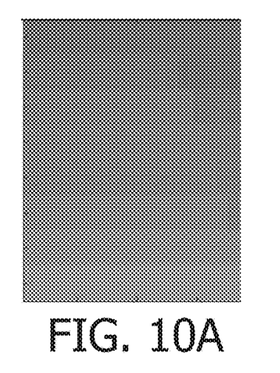
FIGS. 10A to 10E show simulation results obtained from the input velocity field of FIG. 9.

FIG. 10A shows the velocity field input. Discontinuities due to lesion and adjacent structure are only very slightly visible. In case that Eq. 2 would have A, D, c=1; a=0; b=1, then the only effect is a slight enhancement of the visual perception resulting from the sum of the velocities. The difference of the velocities is annulling due to the exponent zero.

Figure 10B:
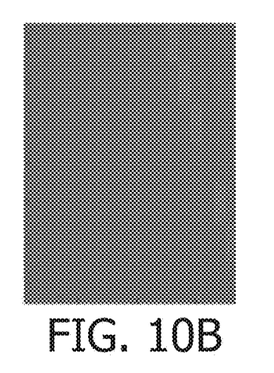

FIG. 10B shows the results when employing the strain rate analogy, i.e., for parameters A, D, a, c=1; b=0. Only the boundary 940 between the two domains (ablated and non-ablated) is slightly distinguishable due to the fact that the difference of the velocities before and after the discontinuities is the same. The sum of the velocities is annulling due to its exponent zero. The weakness of the formulation for the simulated setting can be seen.

Figure 10C:
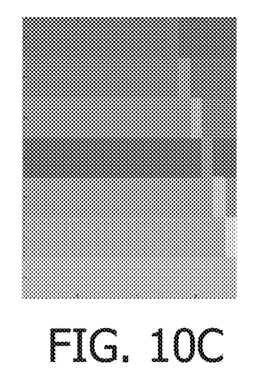

FIG. 10C shows the results when employing Eq. 2 with parameters A, D, a, b, c=1. The differentiating effect of the sum of velocities versus the difference of velocities is illustrated. Both discontinuities, i.e., the second layer 920 as well as the lesion 940, start to become visible in the same dynamic range. Most importantly, the algorithm does not only distinguish the boundary 930 between the domains 910, 920, but the value after the discontinuity is different than before it.

Figure 10D:
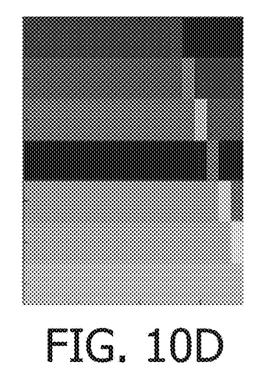

FIG. 10D shows the results when employing Eq. 2 with parameters A, D, a, c=1; b=1.5. Here, the strength of the parameterization of Eq. 2 becomes more pronounced. By taking values of b larger than one, a visual effect is enhanced. Thereby, the dynamic range may be changed in depth.

Figure 10E:
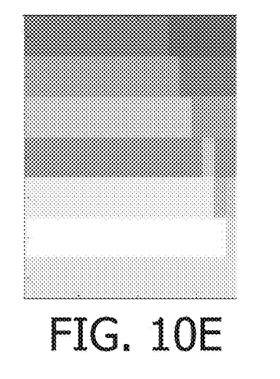

FIG. 10E shows the results when employing Eq. 2 with parameters A, D, c=1; a=0.5; b=1.5. Thus, the exponents do not necessarily need to be positive. Eq. 2 is still preserving similar distinguishing characteristics between domains delimited by discontinuities.

Eq. 2 relates material behavior to applied external load (such as, e.g., thermal, electrothermal, mechanical, cyclical, electromagnetic, radiation, etc. . . . , or combinations thereof). The algorithm may be integrated in real-time software on ultrasound consoles due to taking into account a direct comparison and computation based on subsequent information lines for the velocity field calculation and a specifically tailored Eq. 2 to the desired sensitivity to lesion detection.

Figure 11:
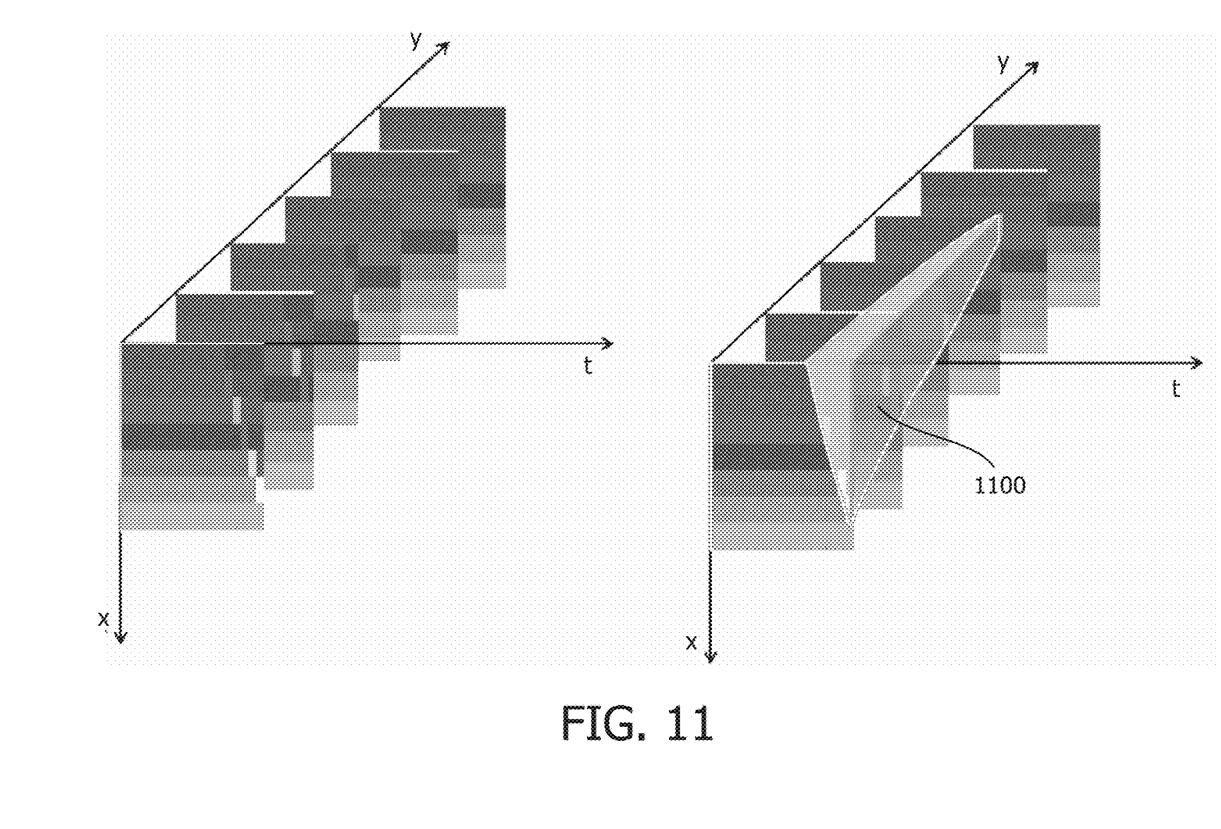
FIG. 11 shows an example to illustrate a visualization of two spatial plus time dimensions.

The invention therefore has potential for using in 2D (two spatial dimensions) and 3D ultrasound based lesion formation imaging, e.g., 2D+time visualization. Visualization of 3D+time is difficult, and would always need to be a cross section of the 3D spatial image and resume to a 2D+time. If the catheter tip comprises B transducers, which are able to create 2D images, the implementation of 2D+time is the logical next step. An example for 2D+time visualization (i.e., visualization of x, y, and t dimensions) indicating ablation lines, as well as an ablation area progression in time 1100 is illustrated in FIG. 11.

Cyclic motion respectively "displacement of structures in time" is apparent in the M-mode images in FIGS. 5, 7, and 8 as longitudinal jitter of the contrast lines. This "jitter" is very visible when the time interval on the full time scale is small, but it is being compressed when the time interval displayed on the time scale is relatively large. Due to the duration of the ablation process of around 60 seconds, or even more, the time scale of the ultrasound window is around the 150 to 180 seconds because the physician would like to have a reference part of the image before the ablation and after the ablation. In these circumstances, the heart beat will show up as a kind of jitter on the ultrasound image, versus a "waviness" when the time interval on the times scale is small. The magnitude of the interaction between catheter and tissue during breathing is influenced by the anatomical location. It could be very visible or not visible at all.

An example application of the invention is any treatment procedure where ultrasound is used for lesion formation monitoring. This includes cardiac ablation monitoring, oncology, and elastography based tissue type differentiation.

The invention can be used in tissue imaging during surgical treatment of cardiac arrhythmias. In these procedures it is desired to create transmural and continuous lesions in order to block electrical activity. In this invention a monitoring apparatus is proposed that uses ultrasound imaging for the direct visualization of the lesion in epicardial ablation. The monitoring apparatus allows using ultrasound imaging for real-time visualization of the progression of the lesion boundary.

This invention can be used in the field of catheter based cardiac ablation. This is especially relevant for catheter treatment of atrial fibrillation. There are at least three different applications for this invention: a) Measurement of heart wall thickness: Support for therapy planning where the ablation energy and duration is based on the measured heart wall thickness; b) Measurement of the lesion after ablation: The purpose is to verify lesion completeness and/or transmurality, when it is still possible for the electrophysiologists to easily go back to the incomplete lesion to add additional ablation points; c) Measurement of the created lesion during ablation. Here, the invention is used for treatment guidance, where the ablation is continued until the lesion measurement indicated that the lesion is continuous and/or transmural.

The invention can be used in tissue imaging during treatment of e.g. cardiac arrhythmias and tumor ablation. In these procedures it is desired to follow the progression of lesion formation during the procedure.

All arrangements located at a catheter tip disclosed above can be used with the monitoring apparatus in accordance with the invention, in particular, with the monitoring apparatus described above with reference to FIGS. 1 and 2.

The monitoring apparatus can comprise any ultrasound unit that allows generating an ultrasound signal depending on received dynamic echo series after ultrasound pulses have been sent out to the object.

Although in the above described embodiments ablation elements are integrated together with an ultrasound unit in a catheter, these embodiments are preferred embodiments only and in another embodiment the monitoring apparatus can comprise a separate catheter including an ultrasound unit, wherein the ablation is performed by using another catheter.

Although in the above described embodiments certain configurations of ultrasound units, ablation elements and/or sensing elements are shown, the invention is not limited to a certain configuration of ultrasound units, ablation elements and/or sensing elements. In an embodiment, the monitoring apparatus does not comprise an ablation element and/or a sensing element. Furthermore, the monitoring apparatus does not even have to comprise an ultrasound unit. In an embodiment, the monitoring apparatus comprises an ultrasound signal providing unit being, for example, a storing unit in which the ultrasound signal is stored or an ultrasound signal receiving unit for receiving the ultrasound signal from an ultrasound unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the discontinuity, of the ablation depth or of a heart wall thickness and/or ablation and/or sensing et cetera performed by one or several units or devices can be performed by any other number of units or devices. For example, the determination of the ablation depth or of the heart wall thickness can be performed by a single unit of by any other number of different units. The determinations and/or the control of the monitoring apparatus in accordance with the above described monitoring method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention relates to a monitoring apparatus for monitoring a structural change in an object, such as a heart wall tissue. Tissue at first and second locations exhibits first and second velocities. The monitoring apparatus comprises an ultrasound signal providing unit for providing ultrasound signals of the object for different times. The monitoring apparatus further comprises a discontinuity determination unit for determining a discontinuity of the first and second velocities based at least in part on a change in time of tissue velocity differences and of tissue velocity sums. From the discontinuity an ablation depth can be determined, which is an important parameter while performing an ablation procedure. For example, it can be used for determining the progress of ablation within the object and for determining when the ablation has reached a desired dimension.

The invention claimed is:

1. A monitoring apparatus for monitoring a structural change in an object, where the object comprises material at first and second locations along a depth direction within the object, where ultrasound signals have a first velocity at the first location of the material, where the ultrasound signals have a second velocity at the second location of the material, the monitoring apparatus comprising:

an ultrasound signal providing unit for providing the ultrasound signals to the object at different times, the ultrasound signals being indicative of the first and second velocities; and a discontinuity determination unit for determining a discontinuity of the first and second velocities based at least in part on a difference between the first velocity and the second velocity at a first time and at a second time, and further based at least in part on a sum of the first velocity and the second velocity at the first time and at the second time.

2. The monitoring apparatus as defined in claim 1, wherein the discontinuity determination unit is configured to determine the discontinuity based at least in part on an expression:

$$(v(t_j,x_i)-v(t_j,x_{i-1}))^a(v(t_j,x_i)+v(t_j,x_{i-1}))^b$$

where $(v(t_j,x_i))$ corresponds to the first velocity at the first location $x_i$ at the first time $t_j$, where $(v(t_j,x_{i-1}))$ corresponds to the second velocity at the second location $x_{i-1}$ at the first time $t_j$, and where b is not equal to zero.

3. The monitoring apparatus as defined in claim 2, wherein
b is equal to or larger than a; and/or
a is less than zero; and/or
b is larger than one.

4. The monitoring apparatus as defined in claim 1, wherein the monitoring apparatus further comprises a velocity determination unit for determining the first and second velocities from the ultrasound signals of the object for different times.

5. The monitoring apparatus as defined in claim 2, wherein the discontinuity determination unit is further configured to determine the discontinuity based at least in part on an expression:

$$\frac{(v(t_j, x_i) - v(t_j, x_{i-1}))^a (v(t_j, x_i) + v(t_j, x_{i-1}))^b}{(x_i - x_{i-1})^c}$$

where c is not equal to zero.

6. The monitoring apparatus as defined in claim 1, wherein the ultrasound signal providing unit comprises an ultrasound unit for
sending ultrasound pulses out to the object,
receiving dynamic echo series after the ultrasound pulses have been sent out to the object,
generating an ultrasound signal depending on the received dynamic echo series.

7. The monitoring apparatus as defined in claim 1, wherein the object is a tissue wall to which energy is applied for influencing the tissue wall such that the ultrasound signal providing unit provides ultrasound signals of the tissue wall for different times.

8. The monitoring apparatus as defined in claim 1, wherein the monitoring apparatus further comprises a sensing probe, in which the ultrasound signal providing unit and an energy application unit for applying energy to the object are integrated.

9. The monitoring apparatus as defined in claim 1, wherein the ultrasound signals represent ultrasound reflection properties of the object at different depths and at different times, wherein the monitoring apparatus further comprises an ablation depth determination unit adapted to determine an ablation depth as the depth of the ultrasound signals at which the discontinuity occurs.

10. The monitoring apparatus as defined in claim 9, wherein the object is a wall, wherein the monitoring apparatus is adapted to determine a thickness of the object and repeatedly the ablation depth, wherein the ablation depth determination unit is adapted to determine repeatedly a degree of transmurality of ablation from the determined thickness and the determined ablation depth.

11. The monitoring apparatus as defined in claim 10, wherein the monitoring apparatus is adapted to terminate an ablation procedure, if a predetermined degree of transmurality of ablation has been reached.

12. The monitoring apparatus as defined in claim 9, wherein the object is a wall, wherein the ablation depth determination unit is adapted to determine the position of a front surface and a back surface of the wall from the ultrasound signals, and wherein the ablation depth determination unit is adapted to determine the thickness of the wall from the determined positions of the front surface and the back surface of the wall.

13. A non transitory computer comprising a monitoring computer program for monitoring a structural change in an object, the monitoring computer program comprising program code, which when executed by a processor, causes a monitoring apparatus as defined in claim 1 to carry out the steps of a monitoring method for monitoring a structural change in the object, where the object comprises material at first and second locations within the object, where the material at the first location exhibits a first velocity, where the material at the second location exhibits a second velocity, when the computer program is ran on a computer controlling the monitoring apparatus, the monitoring method comprising the steps of:

providing ultrasound signals of the object for different times by an ultrasound signal providing unit, the ultrasound signals being indicative of the first and second velocities, determining a discontinuity of the first and second velocities based at least in part on a difference between the first velocity and the second velocity at a first time and at a second time, and further based at least in part on a sum of the first velocity and the second velocity at the first time and at the second time.

* * * * *